United States Patent [19]

Cook

[11] Patent Number: 4,729,369

[45] Date of Patent: Mar. 8, 1988

[54] TOE SPLINT AND BUNION CORRECTION DEVICE

[76] Inventor: Donald E. Cook, Rte. #12, Box 19, Meridian, Miss. 39301

[21] Appl. No.: 876,731

[22] Filed: Jun. 20, 1986

[51] Int. Cl.⁴ ............................ A61F 5/00; A61F 5/37
[52] U.S. Cl. .................................... 128/81 R; 128/153
[58] Field of Search ............................ 128/81 R, 153

[56] References Cited

U.S. PATENT DOCUMENTS

| | | | |
|---|---|---|---|
| 892,412 | 7/1908 | Farra | 128/81 R |
| 2,800,129 | 7/1957 | Swaay | 128/90 |
| 3,219,032 | 11/1965 | Levitt | 128/81 R |

Primary Examiner—Edgar S. Burr
Assistant Examiner—Huong Q. Pham
Attorney, Agent, or Firm—George A. Bode

[57] ABSTRACT

A toe splint and bunion correction device comprising: a substantially L-shaped splint member of a thermoplastic material which maintains rigidity at body temperature; and a velcro fastener for securing the splint member to the foot. The method for preparing and applying the toe splint and bunion correction device comprises the steps of: placing the thermoplastic splint member in a heating medium at a temperature sufficient to allow the splint member to become pliable; removing the splint member from the heating medium; molding the splint member into a configuration accommodating the foot and toe while the splint member is pliable; maintaining the splint member in the configuration accommodating the foot and toe until the temperature of the splint member cools to less than the temperature at which it became rigid; and, fastening the splint member to the foot with a velcro fastener.

5 Claims, 3 Drawing Figures

TOE SPLINT AND BUNION CORRECTION DEVICE

BACKGROUND OF THE INVENTION

1. Field of the Invention

The present invention relates to new and useful improvements in toe splints and bunion correction devices and methods of application of the same. The present invention relates more particularly, to such a device comprising a thermoplastic splint and removable fastening means, and to a method which includes the molding of a themoplastic splint for custom fitting each patient and condition.

2. General Background

Treatment of a bunion by the medical profession most frequently requires the great toe be held in a position wherein the bones in the toe are in proper alignment.

Since the procedure often involves surgery, it is very important that the device to be used for holding the great toe in proper position be amenable to easy cleaning and not provide an environment conducive to the spread of infection.

It is also desirable, because of the many different sizes and shapes of feet to be treated, that the device for holding the great toe in position be readily adjustable to a wide variety of sizes and shapes.

When surgery is required, the device for holding the great toe in position must fit around the surgical dressing. And swelling may also result in changes in the size and shape of part of the foot. For the aforementioned reasons it is necessary in the present state of the art to maintain a large inventory of such devices on hand in order to appropriately fit all of the different sizes, shapes and conditions.

A bunion may cause the great toe to lie either over or under the second toe, making it desirable that the device for holding the great toe in position have the capacity for correcting this vertical deviation by holding the great toe at differing angles from the horizontal plane of the foot.

Various attempts have been made to fill the need for such a device. For example:

U.S. Pat. No. 1,785,185 issued to J. C. Day provides a foot encircling band and a toe encircling band having a pocket for a pad which serves to seperate the great toe and second toe;

U.S. Pat. No. 2,190,016 issued to J. C. Day, et al. provides both a toe and foot encircling band with a pocket of larger relative dimensions for padding which provides metatarsal support and gentle pulling action to cause the joint and toe to assume their normal positions;

U.S. Pat. No. 2,596,038 issued to M. B. Mayer provides a pocket for the great toe which is held in place by a plurality of straps;

U.S. Pat. No. 2,958,324 issued to W. Berkemann provides for a lever, one end of which can be made to exert pressure on the inside surface of the great toe by tightening the other end of the lever by an adjustable strap, the fulcrum being held in position by elastic webbing attached partially around the foot;

U.S. Pat. No. 1,175,718 issued to B. Crowe provides a solid member having a pocket for the great toe which is held in place by a securing strap;

Canadian Pat. No. 704,642 provides a unitary piece with a loop for the toe and a cushioning strip near the other end which wraps around the foot;

U.S. Pat. No. 1,665,030 issued to M. Hartwig provides for a solid member having a pocket for the great toe and secured by encircling the heel;

U.S. Pat. No. 3,219,032 issued to M. R. Levitt provides for two interconnected solid members, one of which has a loop for encircling the toe, the other fitting around the heel; and U.S. Pat. No. 2,589,791 issued to W. W. Fine provides for a solid member fitting around part of the foot and having a loop for the great toe.

Although these patents have attempted to fill this need, until now none has been completely successful in providing a device which is easily modifiable to accomodate surgical dressing, to fit all shapes, sizes, and conditions, that has the capacity for holding the toe at differing angle from the horizontal plane of the foot, and which by reason of material of construction and surface texture is extremely easy to clean, to sterilize, and to maintain in a sterile condition.

Accordingly, there appears to be a longstanding need for an improved device which will overcome the aforementioned problems.

SUMMARY OF THE PRESENT INVENTION

The present invention relates to a toe splint and bunion correction device which comprises a thin substantially L-shaped splint member of a thermoplastic material which maintains rigidity at normal body temperature and has an elongated base member for engaging the foot and a toe encircling member integrally formed with and perpendicular to the base member for encircling one of the toes of the foot when the splint member is subjected to a predetermined temperature above normal body temperature and means for removably fastening the splint member to the foot including a band having velcro portions thereon passed around the foot so as to mate the portions when the band overlaps itself. As the condition of the foot/toe improves, or as medical factors indicate, the splint member, because it is constructed of a thermoplastic material, can be easily remolded to accomodate any change of configuration which may be necessary by simply reheating it to a temperature above the predetermined pliable point. As the splint member again cools below this point it once again becomes rigid, thereby providing the needed support.

The preferred embodiment of the apparatus of the present invention solves the aforementioned problems in a straightforward and simple manner. What is provided is a new and useful improvement in toe splints and bunion correction devices, and methods of application of the same.

The present invention has as its primary objective the efficient and effective medical treatment of bunions and the alleviation of human suffering relating thereto.

Another important objective of the present invention is to provide a device for holding the great toe in the necessary position for proper bone alignment.

Still another important object of the present invention is to provide a device for holding the great toe at a predetermined angle from the horizontal plane of the foot.

Yet another important object of the present invention is to provide a device which by reason of material of construction and surface texture is easily cleaned, sterilzed and maintained in a sterile condition, thereby discouraging the spread of infection.

Still another important object of the present invention is to provide a device for medical treatment of stable fractures of the great toe, the distal portion of the first metatarsal, or any condition in which non-rigid immobilization of the great toe is desirable.

Yet another object of the present invention is to provide a device which can be used in the medical treatment of similar conditions of the little toe, or any other toe.

Still another important object of the present invention to provide a device for the medical treatment of the aforementioned conditions which is easily adaptable to a wide variety of sizes and shapes of patients' feet, and which can easily accomodate changes in contours due to surgical dressings, swelling, and other conditions, thereby avoiding the difficulties of maintaining large stocks of treatment devices, thereby increasing the efficiency of medical treatment.

Other objects, advantages and novel features of the present invention will become apparent from the following detailed description and drawing.

BRIEF DESCRIPTION OF THE DRAWING

For a further understanding of the nature and objects of the present invention, reference should be had to the following detailed description taken in conjunction with the accompanying drawing in which like parts are given like reference numerals and, wherein.

DETAILED DESCRIPTION OF THE PREFERRED EMBODIMENT

Figure 1:
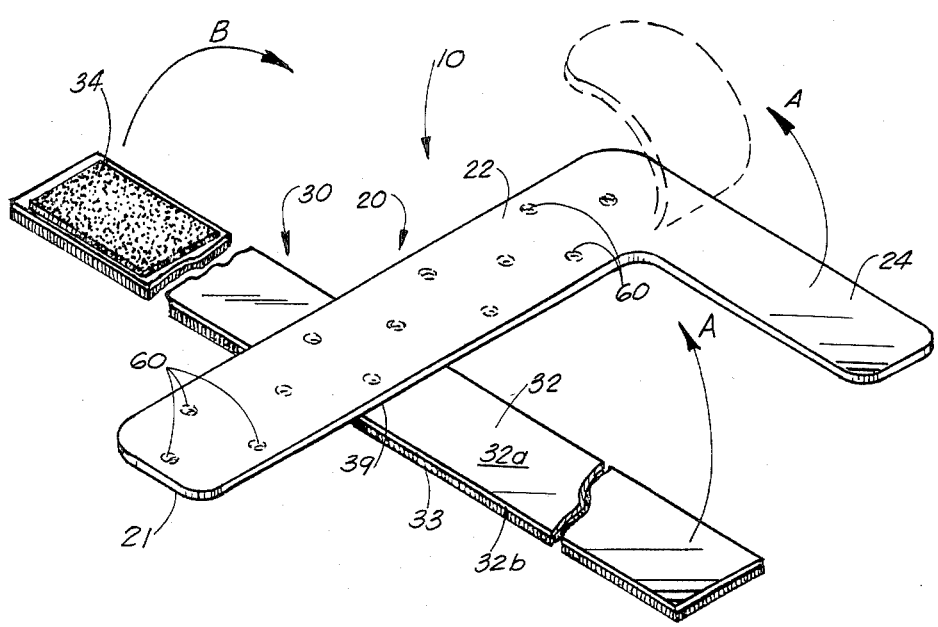
FIG. 1 is a perspective view of the preferred embodiment of the apparatus of the present invention.

Referring now to the drawing, and in particular FIG. 1, the apparatus of the present invention is designated generally by the numeral 10. Toe splint and bunion correction device 10 is generally comprised of a splint member 20 and flexible fastening means 30. Splint member 20 is generally L-shaped, having an elongated base section 22 and an integrally formed toe encircling section 24, generally shorter than base section 22 and perpendicular thereto so as to complete the "L." Splint member 20 is constructed from any suitable thermoplastic material (defined as any material which becomes soft and pliable whenever it reaches or exceeds a certain temperature, the temperature determined by the characteristics of the material, i.e., polyethylene) which is rigid at body temperature (approximately 98.6° F. (37.0° C.)), but which becomes pliable at approximately 135° F. (57.2° C.)—its "softening point."

It is necessary that splint member 20 maintain rigidity at body temperature, but the temperature at which it becomes pliable—the "softening point"—is not critical, to the extent it is substantially greater than 98.6° F. (37.0° C.).

Thermoplastic materials which become pliable at different temperatures (that is, have different "softening points") may be selected by those skilled in the art for different applications. In this embodiment, and for illustration purposes only, one is chosen which loses rigidity at or has a "softening point" of approximately 135° F. (57.2° C.) so splint member 20 has the necessary rigidity at body temperature, yet can be molded into the desired configuration at a temperature which can be manually handled comfortably.

In an alternate embodiment, splint member splint member 20 may be constructed so as to have a multiplicity of spaced apart perforations 60 therein (shown in phantom view in FIG. 1) so as to promote air circulation and cooling.

Figure 2:
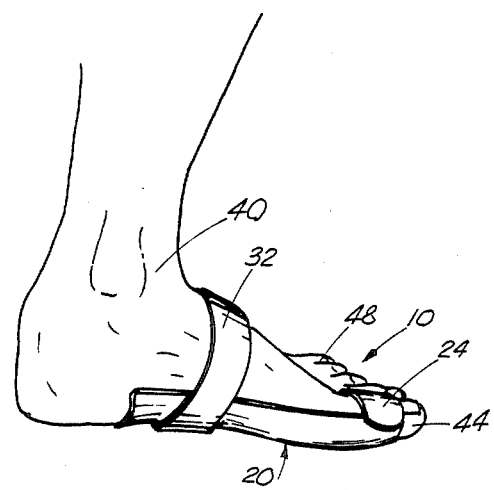
FIG. 2 is a perspective view of the preferred embodiment of the apparatus of the present invention applied in treatment of a bunion or other condition to hold the great toe in proper bone alignment.
Figure 3:
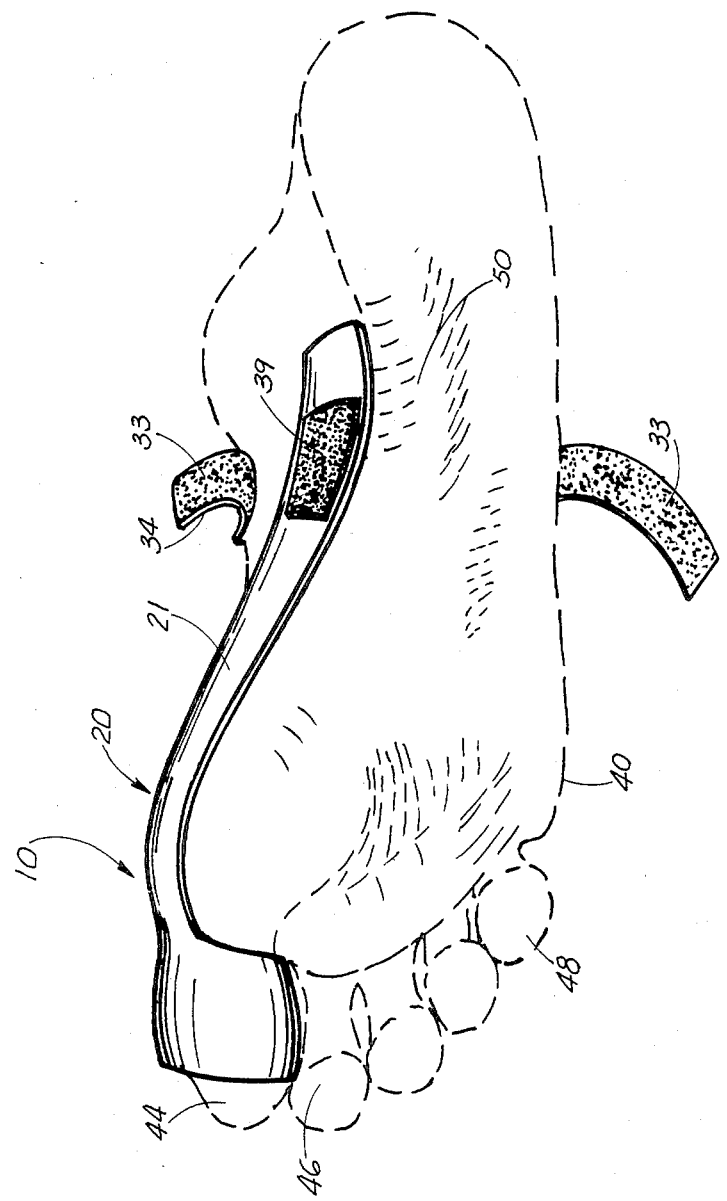
FIG. 3 is a bottom view of an alternate method of fastening the apparatus of FIG. 1 to the foot in which the splint has been molded to custom fit the foot and hold the great toe in the proper position, and, further showing the fastening band only partially encircling the foot.

Fasetening means 30 which may be applied in one of two methods, as best seen in FIGS. 1 (preferred method of fastening) and 3 (alternate method of fastening), is shown to include a velcro fastening portion 39 adhesively mounted on the underside 21 of base section 22 of splint member 20, a flexible band 32 and a velcro fastener portion 34 adhesively mounted on one end of the upper surface 32a of band 32. Band 32 has its entire under surface 32b provided with velcro 33, and preferrably the female (loop) portion thereof. Fastener portion 34 is a patch of velcro, and preferrably the male (hook) portion thereof. Fastening means 30 can be applied to secure base section 22 of splint member 20 to the foot 40, as best seen in FIG. 2, by wrapping band 32 around splint member 20 (in the directions of ARROWS A and B) after it has been applied to foot 40 and by merely pressing the male fastener portion 34 against female fastener portion 33 at the desired location therealong to accomodate foot 40. Fastener means 30 can also be applied to secure base section 22 of splint member 20 to the foot 40 in an alternate method, as best seen in FIG. 3 (band 32 is reversed from FIGS. 1 and 2, "upper surface" 32a becomes the "under surface" and "under surface" 32b becomes the "upper surface"), by wrapping band 32 around splint member 20 after velcro fastner portion 33 is pressed against fastner portion 39 which has been adhesively mounted on the underside 21 of splint member 20 and then merely pressing the female fastener portion 33 against male fastener portion 34 at the desired location along fastener portion 33 to accomodate foot 40. 0f course, other equivalent fastening means can also be used.

In operation, splint member 20 is placed in any conventional heating medium such as water having a temperature of not less than approximately 140° F. (60° C.). As the temperature of splint member 20 then increases, its thermoplastic property causes it to become pliable. It is then removed from the water or other heating medium and can be easily molded into the desired configuration to accomodate foot 40. Splint member 20 may then be allowed to cool slightly before molding so as to increase the comfort of manual handling.

During the molding operation splint member 20 is shaped to custom-fit the patient's foot 40. Splint member 20 can also easily be shaped so as to accomodate a surgical dressing or swelling. Toe encircling section 24 of splint member 20 is molded around the great toe 44 so as to hold it in the desired position. Toe encircling section 24 of splint member 20 is, in the preferred method of application, passed under the bottom of the great toe 44 (FIGS. 1 and 3 illustrating application to the right foot and FIG. 2 illustrating application to the left foot), and then over the top of it in the direction of ARROWS A (FIG. 1), so as to completely encompass and provide support for great toe 44. Alternatively, although not shown in the drawing, splint member 20 can be reversed and toe encircling section 24 can be passed over the top of great toe 44 first, and then around the bottom so as to fully encircle and provide support for the great toe 44.

After splint member 20 has been molded to custom fit the patient's foot 40 and to hold great toe 44 in the desired position, it is then held in place a short while until the thermoplastic material cools sufficiently below the "softening point" to become rigid. Splint member 20 can then be further custom-fitted to the configuration or condition of a patient's foot by trimming the base section 22 or the toe encircling section 24 with ordinary heavy shears.

A paper backing (not shown) is then removed from the velcro fastener portions 33 and 34 (and 39 if the method of fastening of FIG. 3 is adopted) which can then be applied to splint member 20, as best seen in FIG. 2 in the preferred fastening method and in FIG. 3 in the alternate fastening method. Velcro fastener 34 is normally applied at a position on splint member 20 corresponding to the mid-point of the arch 50 of foot 40. In the preferred fastening method of FIGS. 1 and 2, band 32 is then passed around foot 40 and as it overlaps itself, fastener portion 34 is pressed against fastener portion 33 on under surface 32b of band 32 and thus secures fastener means 30 around base section 22 of splint member 20 and foot 40. Fastener means 30 can be custom-fitted by trimming the excess of band 32 which, when secured, extends beyond fastener portion 34. In the alternate fastening method, band 32 is reversed from the orientation of FIGS. 1 and 2 to that of FIG. 3 and fastener portion 33 is pressed against fastener portion 39 adhesively mounted on splint member 20. The band 32 is then passed around foot 40 and as it overlaps itself, fastener portion 33 is pressed against fastener portion 34 on the "upper" surface 32a of band 32 and thus secures fastener means 30 around base section 22 of splint member 20 and foot 40. Custom fitting by trimming the excess of band 32 is as in the preferred fastening method.

My toe splint and bunion correction device 10 can also be used in treating stable fractures of the great toe 44 or distal portion of the first metatarsal, or any condition in which non-rigid immobilization of the great toe 44 is desirable.

My toe splint and bunion correction device 10 can also be used for treating similar conditions of the second toe 46 or the little toe 48.

With appropriate lengthening of the toe encircling section 24 of the splint 20, my toe splint and bunion correction device can be used for treating similar conditions of any of the toes on a patient's foot 40.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A toe splint and bunion correction device comprising:
    (a) a thin substantially L-shaped splint member of a thermoplastic material which maintains rigidity at normal body temperature, and having an elongated base member for engaging and supporting the foot and a toe encircling member integrally formed with and substantially perpendicular to said base member for encircling one of the toes of said foot when said splint member is subjected to a predetermined temperature greater than said normal body temperature; and
    (b) means for removably fastening said splint member to said foot, wherein said fastening means comprises a band removably wrappable about said foot and said splint member, and having first means attached to one side of said band, and extending the length thereof, for reciprocally mating and engaging second means attached to one end portion of the opposite side of said band when said band overlaps itself.

2. The apparatus of claim 1, wherein said thermoplastic splint member becomes pliable at a temperature substantially greater than said normal body temperature.

3. The apparatus of claim 1, wherein said thermoplastic splint member becomes pliable at a temperature of approximately 135° F. (57.2° C.).

4. The apparatus of claim 1, wherein said fastening means further comprises third means attached to an intermediate portion of the underside of said base member for reciprocally mating and engaging said first means.

5. The apparatus of claim 1, wherein said splint member has a multiplicity of spaced apart perforations provided therein.

* * * * *